(12) United States Patent
Lorraine et al.

(10) Patent No.: US 8,054,470 B2
(45) Date of Patent: Nov. 8, 2011

(54) METHOD AND APPARATUS FOR SPECTROSCOPIC CHARACTERIZATION OF SAMPLES USING A LASER-ULTRASOUND SYSTEM

(75) Inventors: Peter W. Lorraine, Niskayuna, NY (US); Thomas E. Drake, Jr., Fort Worth, TX (US); John B. Deaton, Jr., Niskayuna, NY (US); Marc Dubois, Keller, TX (US); Robert Filkins, Niskayuna, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 749 days.

(21) Appl. No.: 12/120,907

(22) Filed: May 15, 2008

(65) Prior Publication Data

US 2009/0284752 A1 Nov. 19, 2009

(51) Int. Cl.
*G01B 9/02* (2006.01)
(52) U.S. Cl. ....................................... 356/502
(58) Field of Classification Search .................. 356/502, 356/237.1–241.6
See application file for complete search history.

(56) References Cited

U.S. PATENT DOCUMENTS

| 6,041,020 | A | 3/2000 | Caron et al. | |
| 6,335,943 | B1 * | 1/2002 | Lorraine et al. | 372/28 |
| 6,668,654 | B2 * | 12/2003 | Dubois et al. | 73/643 |

FOREIGN PATENT DOCUMENTS

| WO | 0107906 A1 | 2/2001 |
| WO | WO 01/07906 A1 | 2/2001 |
| WO | 0218958 A2 | 3/2002 |
| WO | WO 02/18958 A2 | 3/2002 |

OTHER PUBLICATIONS

Dubois et al., "Experimental verificaton of the effects of optical wavelength on the amplitude of laser generated ultrasound in polymer-matrix composites", Ultrasonics 40 (2002), pp. 809-812.
Dubois et al., "Experimental comparison between optical spectroscopy and laser-ultrasound generation in polymer-matrix composites", Applied Physics Letter, vol. 79, No. 12, Sep. 17, 2001, pp. 1813-1815.
Dubois et al., "Progress on the Development of an Advanced Laser Ultrasound Generation Source for Inspecting Polymer-Matrix Composites", CP615, Review of Quantitative Nondestructive Evaluation vol. 21, ed. by D.O. Thompson and D. E. Chimenti, American Institute of Physics (2002), pp. 300-307.
The International Search Report and the Written Opinion for PCT/US2009/043906 Dated May 14, 2009. C. Edwards, et al.; Laser Generated Ultrasound: et al: "IEE Proceedings—Science, Measurement and Technology"; IEE Proceedings: Science, Measurement and Technology, IEE, Stevenage, Herts, GB, vol. 148, No. 4, Dated Jan. 1, 2001; pp. 129-142.
Guilliorit E et al.: "Laser Ultrasonic Technology in Europe for Innovative Inspection of Aircraft Strucutres"; 16th World Conference on NDT, Dated Jan. 1, 2004; pp. 1-8.
European Office Action dated Apr. 4, 2011 issued in EP Application Serial No. 09 747 550.3 (4 pages).

* cited by examiner

*Primary Examiner* — Hwa Lee
(74) *Attorney, Agent, or Firm* — Bracewell & Giuliani LLP

(57) ABSTRACT

A method of spectroscopic analysis of a material using a laser ultrasound system. The method includes measuring amplitude displacement of a target surface that has been excited with a generation laser. The amplitude displacements relate to the target's optical absorption properties. Amplitude displacements are generated over a range of laser wavelengths to obtain an optical absorption signature useful to identify the target material characteristics.

14 Claims, 2 Drawing Sheets

METHOD AND APPARATUS FOR SPECTROSCOPIC CHARACTERIZATION OF SAMPLES USING A LASER-ULTRASOUND SYSTEM

BACKGROUND

1. Field of Invention

The invention relates generally to the field of non-destructive testing. More specifically, the present invention relates to a method and system for spectroscopic analysis using a laser-ultrasound system.

2. Description of Prior Art

Recent developments in creating composite materials have expanded the use of composite materials into a wide variety of applications. Because of its high strength and durability combined with its low weight, composites are replacing metals and metal alloys as the base material for certain load bearing components. For example, composites are now commonly used as a material for body parts and structure in vehicles such as automobiles, watercraft, and aircraft. However, to ensure composite mechanical integrity, strict inspections are required. The inspections are typically required upon fabrication of a component made from a composite and periodically during the life of the component.

Laser ultrasound is one example of a method of inspecting objects made from composite materials. The method involves producing ultrasonic vibrations on a composite surface by radiating a portion of the composite with a pulsed generation laser. A detection laser beam is directed at the vibrating surface and scattered, reflected, and phase modulated by the surface vibrations to produce phase modulated light. Collection optics receives the phase modulated laser light and directs it for processing. Processing is typically performed by an interferometer coupled to the collection optics. Information concerning the composite can be ascertained from the phase modulated light processing, the information includes the detection of cracks, delaminations, porosity, foreign materials (inclusions), disbonds, and fiber information.

One of the advantages of using laser ultrasound for objects with a complex shape, such as components used in aerospace, is a couplant is unnecessary and the complex shaped can be examined without contour-following robotics. Laser-ultrasound can be used in aerospace manufacturing for inspecting polymer-matrix composite materials. These composite materials may undergo multiple characterization stages, one of which is the ultrasonic inspection by laser-ultrasound. At some point during manufacturing these composites must be chemically characterized to ensure the resins used in forming the composite are properly cured. Additionally, it is important to determine that the correct resins were used in the forming process. Composite chemical characterization typically involves obtaining control samples for infrared spectroscopy laboratory analysis.

SUMMARY OF INVENTION

Disclosed herein is a method of material analysis comprising directing a generation laser beam at target surface to create ultrasonic displacements on a target surface, where the generation laser wavelength is identifiable, measuring the target surface displacement amplitude for the identifiable laser wavelength, varying the laser wavelength, and determining the target surface composition by comparing the relative measured ultrasonic signal amplitudes at specific laser wavelengths to the relative ultrasonic signal amplitude of a known compositions at the same generation laser wave wavelengths. The spectroscopic method may further include evaluating the target surface structural integrity using the measured target surface displacement amplitude. The target may be a manufactured part and may be assembled onto a finished product. The method can further involve measuring surface ultrasonic displacement amplitudes at discrete wavelengths over a range of wavelengths for the target, forming a measured array of data correlating the measured target surface displacement amplitudes for the discrete wavelengths, and comparing the measured array of data to an array of data of displacement amplitudes and discrete wavelengths for a material of known composition to determine the target composition. Optionally, the method may include producing a comparison data array of values of measured amplitudes of target surface displacement correlated to the wavelengths of the laser wave that created the displacement, where the target surface composition is known. The measured displacement amplitude may be compared to the data array to determine the target composition from the comparison. The measured data array may be created by measuring target surface displacement amplitudes over a range of known laser wavelengths then comparing the measured data array to the comparison data array, to determine the target composition from the comparison. The finished product may comprise an aircraft. The target composition may include resin and the method may further include ensuring the resin is properly cured by the step of determining the target surface composition and may also include confirming a particular resin is present in the target by the step of determining the target surface composition. The target surface may include a coating.

Also disclosed herein is a method of analyzing an object by (a) generating an ultrasonic displacement on the object using a pulsed generation laser beam operating at more than one known wavelength, (b) measuring the displacement amplitude generated at each known wavelength, (c) creating a measured data array comprising the displacement amplitude generated at each known wavelength and the corresponding known wavelengths, (d) comparing the measured data array to a data array obtained from a known material, and (e) identifying the object composition based on the step of comparing the measured data array to the data array. The data array may be obtained from a known material and created by generating ultrasonic displacement in a sample of the known material using a generation laser over a range of wavelengths, measuring the displacements, and correlating the displacements to the laser wavelength. The data array obtained from a known material may be created by any standard spectroscopic method; for example, FTIR transmission or photoacoustic methods. The object may also be a manufactured part and may be affixed to an aircraft. The present disclosure further includes a method of ultrasound inspection of a target object where a generation laser beam is directed onto the target object, ultrasonic displacements are generated on the target object with the generation laser beam, the ultrasonic displacements are measured, the generation laser beam wavelength is varied, additional ultrasonic displacements on the target object are created with the generation laser beam operating at a different laser beam wavelength, the additional ultrasonic displacements are measured, a measured data array of ultrasonic displacements and generation laser beam wavelengths is formed, the measured ultrasonic displacements are correlated to the wavelength of the generation laser beam used to generate the displacement, the measured data array is compared to a data array of a known material, the target object material is identified based on the step of comparing, and defects in the target object are detected by analyzing the ultrasound displacements. These steps may be accomplished by scanning a substantial amount of the target object with the generation laser beam. The target object may be a part assembled within a finished product.

BRIEF DESCRIPTION OF DRAWINGS

Some of the features and benefits of the present invention having been stated, others will become apparent as the description proceeds when talken in conjunction with the accompanying drawings, in which.

Figure 1:
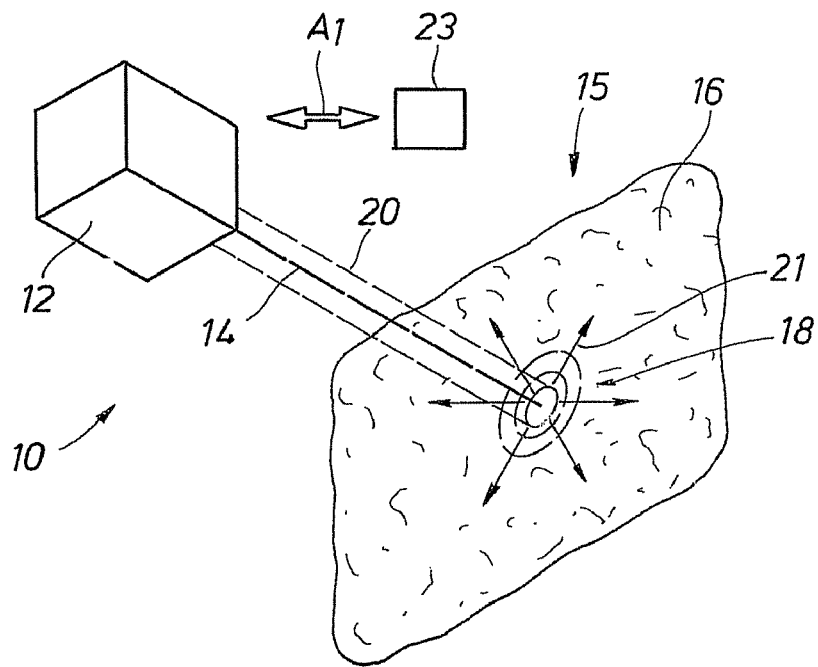
FIG. 1 is a perspective view of an ultrasonic inspection system.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The present invention will now be described more fully hereinafter with reference to the accompanying drawings in which embodiments of the invention are shown. This invention may, however, be embodied in many different forms and should not be construed as limited to the illustrated embodiments set forth herein; rather, these embodiments are provided so that this disclosure will be thorough and complete, and will fully convey the scope of the invention to those skilled in the art. Like numbers refer to like elements throughout. For the convenience in referring to the accompanying figures, directional terms are used for reference and illustration only. For example, the directional terms such as "upper", "lower", "above", "below", and the like are being used to illustrate a relational location.

It is to be understood that the invention is not limited to the exact details of construction, operation, exact materials, or embodiments shown and described, as modifications and equivalents will be apparent to one skilled in the art. In the drawings and specification, there have been disclosed illustrative embodiments of the invention and, although specific terms are employed, they are used in a generic and descriptive sense only and not for the purpose of limitation. Accordingly, the invention is therefore to be limited only by the scope of the appended claims.

FIG. 1 provides a side perspective view of one embodiment of a laser ultrasonic detection system 10. The detection system 10 comprises a laser ultrasonic unit 12 formed to emit a generation beam 14 and directed to an inspection target 15. The generation beam 14 contacts the inspection target 15 on an inspection surface 16. The generation beam 14 thermo-elastically expands the inspection surface 16 to produce corresponding wave displacements 18 on the inspection surface 16. In one embodiment, the generation beam 14 is a pulsed laser configured to produce the ultrasonic displacements 18 on the inspection surface 16. A detection beam 20 is also illustrated emanating from the laser ultrasonic unit 12 and is shown coaxial around the generation beam 14. Although emanating from the same laser ultrasonic unit 12, the detection and generation beams (14, 20) are generated by different sources. However, the detection beam 20 may optionally originate from a different unit as well as a different location. As is known, the detection beam 20 comprises a detection wave that is scattered, reflected, and phase modulated upon contact with the ultrasonic displacements 18 to form phase modulated light 21. The phase modulated light 21 from the detection beam 20 is then received by collection optics 23 and processed to determine information about the inspection target 15. The generation and detection beams (14, 20) may be scanned across the target 15 to obtain information regarding the entire surface 16. A mechanism (not shown) used to scan the beams (14, 20) may be housed within the laser ultrasonic unit 12. A processor (not shown) for controlling the mechanism and optionally for processing the data recorded by the collection optics, may also be housed in the laser ultrasonic unit 12. The collection optics 23 are shown separate from the laser ultrasonic unit 12 and in communication with the laser ultrasonic unit 12 through the arrow A, however the collection optics may be included with the laser ultrasonic unit 12.

Disclosed herein is a method of ultrasonically inspecting a target object for defects using a laser ultrasonic testing system and using the laser ultrasonic testing system to also spectroscopically characterize the target object. In one embodiment of the present method, a generation beam is formed by a laser ultrasound system and directed to the target object to produce thermo-elastic expansions on the surface of the target. Ultrasonic displacements are created on the target surface in response to the thermo-elastic expansions. It has been discovered that the amplitude of the ultrasonic displacement, at certain ultrasonic wavelengths, is directly proportional to the optical penetration depth of the generation laser beam into the target surface. The optical penetration depth is the inverse of the optical absorption of the target. Accordingly, by varying the generation laser beam optical wavelength, an absorption band of the target material can be observed over a wavelength range of the generation beam.

In one embodiment of the method described herein, a generation laser beam, such as from the laser ultrasonic source 12 of FIG. 1, is directed at a target 15 to create ultrasonic displacements 18 on the target surface 16. The amplitudes of the ultrasonic displacements 18 may be measured by the detection laser beam 20 as described above. The wavelength of the generation laser beam 14 should be identifiable, that is, the wavelength will be known when producing the surface ultrasonic displacements, can be calculated, or otherwise discerned. The target 15 material can be identified by correlating the measured surface displacement 18 with the wavelength of the generation beam 14 used to create the surface displacement 18. The values for displacement and wavelength can be compared to previously recorded or otherwise obtained plots or data arrays of corresponding displacement amplitude and generation beam wavelength of known materials. Thus matching measured relative amplitude and wavelength values with reference relative amplitude and wavelength values of a known material, the target material and/or composition is determinable. In one embodiment of the present method, a single measurement of displacement amplitude with a corresponding generation beam wavelength is used for identifying a test object material.

In one optional embodiment, the detection beam wavelength is varied over a spectral range and at discreet points along the range ultrasonic displacements are created in the object. The displacement values at each discreet wavelength are measured and correlated to the generation beam wavelength used to create the displacement. The measured displacement values and the discreet wavelength values are used to populate a data array of measured values. Similarly, the measured data array can be compared and matched to a data array comprising generation beam wavelengths and corresponding displacements of a known material or materials to thereby identify the target material. In another embodiment of the present method, two measurements of displacement amplitude with a corresponding generation beam wavelength are used for identifying a test object material. In yet another embodiment of the present method, more than two measurements of displacement amplitude with a corresponding generation beam wavelength are used for identifying a test object material. In yet another embodiment of the present method, multiple measurements of displacement amplitude with a corresponding generation beam wavelength are used for identifying a test object material, where the spectral range of the generation beam wavelength is from about 0.1 microns to about 20 microns, optionally from about 0.5 microns to about 15 microns, optionally from about 1 micron to about 10 microns, optionally about 2 microns to about 8 microns, optionally about 2.5 microns to about 7.5 microns, and optionally about 3 microns to about 4 microns. In another embodiment, the increment between successive generation beam wavelengths may be about 0.01 microns or about 3 microns, or any value between. Optionally, successive wavelength values may vary.

One of the many advantages of employing the present method is the spectroscopic analysis described herein may be performed on parts that have been manufactured instead of a sample taken from the particular part and analyzed in a laboratory. Additionally, the spectroscopic analysis described herein can also be employed when the part is affixed to a finished product. Optionally, the present method may be used on a finished product during the period of its useful life, i.e. after having been put into service. For example, the spectroscopic analysis can occur on an aircraft part during the acceptance testing of the part prior to its assembly on the aircraft. Similarly, after being affixed onto the aircraft, a part can be analyzed using the spectroscopic analysis, prior to acceptance of the aircraft, or after the aircraft has been in service and during the life of the part or of the aircraft.

It should be pointed out however the present method is not limited to final products comprising aircraft, but can include any product comprising two or more parts. Additionally, the laser ultrasonic system can be used to provide spectroscopic analysis of parts or portions of parts in hard to access locations. Not only can the present method determine the composition of a target object, such as a manufactured part, the method can determine if the object forming process has been undertaken correctly. For example, if the part is a composite or comprised of a resin product, it can be determined if the composite constituents, such as resin, have been properly processed or cured. Additionally, it can also be determined if a particular or desired constituent, such as resin, was used in forming the final product. The analysis can also determine if a coating, such as a painted surface, has been applied to an object, and if the proper coating was applied to the surface and applied properly.

Figure 2:
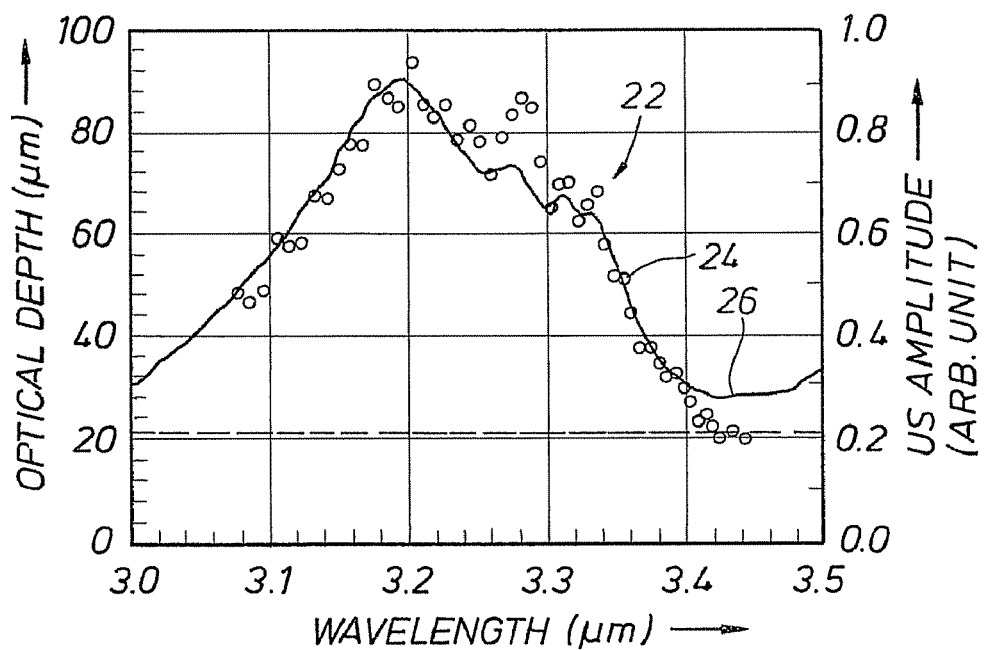
FIGS. 2-4 include graphic plots comparing measured optical depth and displacement amplitude of a composite.

With reference now to FIG. 2, this figure illustrates a comparison of optical penetration depth and ultrasonic amplitude displacement (ordinate) versus the optical wavelength (abscissa) of the source used to create the penetration depth and displacement. More specifically, FIG. 2 illustrates a plot 22 reflecting actual data recorded while testing a graphite-epoxy sample. The plot 22 comprises a series of points 24 that represent measured amplitudes of ultrasonic displacements of the graphic epoxy sample correlated to the generation beam wavelength that created the ultrasonic displacements. The measured optical depth was obtained by a photo acoustic evaluation and it is represented by the line 26. The units of measured optical depth and wavelength are both in microns. In FIG. 2, the values of amplitude of the ultrasonic displacements were normalized to clearly illustrate the proportional relationship between the measured amplitude and the optical penetration depth. In FIG. 2, the absolute values are indicative of the displacement response, the relative shapes of line 26 and of the series of points 24 can be used to identify the material of the target. Moreover, a limited number of points can be used for a measurement. For example, the ratio of the ultrasonic amplitudes measured at two given wavelengths can be used to either identify the target material or a specific characteristic like the level of curing.

Accordingly, recorded optical depth data of known composites provides a valid comparison reference to identify a material from measured ultrasonic displacement values and corresponding generation beam wavelength. As noted above, the identification with regard to the material is not limited to the material composition, but can also include coatings, if the material had been properly processed, and percentages of compositions within the materials.

Figure 3:
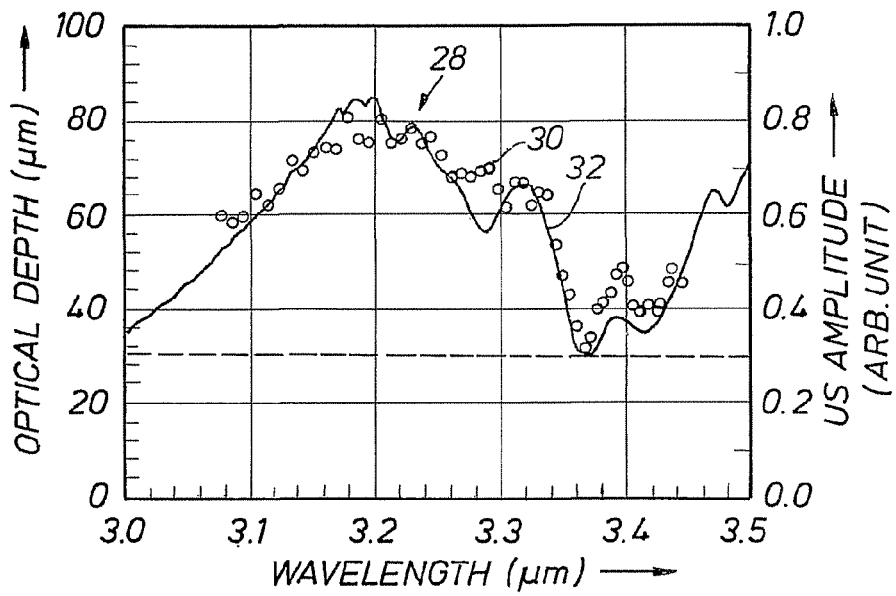
Figure 4:
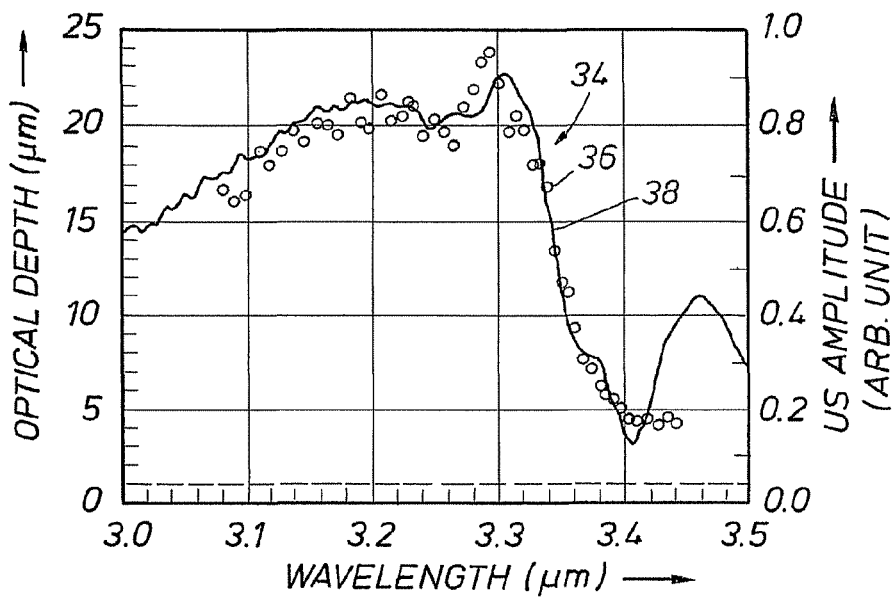

FIG. 3 also illustrates a plot 28 comparing normalized points 30 representing measured amplitude displacements produced by a generation beam and a corresponding line 32 reflecting measured optical depth. In this example the material was a graphite-BMI sample. FIG. 4 also compares measured optical depth to normalized amplitude data over a given wave length. In the example of FIG. 4, the object comprises a painted graphite epoxy sample.

In FIGS. 2-4, a comparison was presented between a known spectroscopic technique, photoacoustics, and laser ultrasound measurements at 2.5 megahertz. The photo acoustic measurements were performed in a laboratory on small samples that were five millimeters in diameter cut from the composite parts. The laser ultrasound measurements were performed directly on the composite parts themselves. The laser ultrasound measurements were obtained with a laser ultrasound system equipped with an optical parametric oscillator allowing wave length tuning between 3.0 and 3.5 microns. This wavelength range corresponds to the stretching mode of the C—H molecular bond. FIGS. 2-4 clearly illustrate the proportional relationship between ultrasonic displacement and optical depth in a material, thereby illustrating another advantage of material analysis using the present method. The results also show that the laser ultrasound measurements allow easy differentiation between different types of materials.

A more complete analysis can employ ultrasonic amplitude at several frequencies other than 2.5 MHz, thus the present method is not limited to measurements at 2.5 MHz. The use of several ultrasonic frequencies or of the broadband ultrasonic signal; while more complicated, is included within the scope of the method described herein.

Another advantage of the present method is a laser ultrasound detection system can perform target spectroscopic analysis while at the same time analyzing the bulk material for the presence of defect conditions and measuring other general material characteristics such as: delaminations, porosity, foreign materials (inclusions), disbonds, cracks, fiber characteristics such as fiber orientation and fiber density, part thickness, and bulk mechanical properties. In addition to the savings of time and capital, a more representative spectroscopic analysis is achievable since the analysis is performed on the object itself instead of a test coupon or control sample. As noted above, the scan can be performed on a manufactured part by itself, the part affixed to a larger finished product, or the final finish assembled product as a whole.

Changing generation beam wavelength can be accomplished in several ways. For example, an optical parametric oscillator can be included to provide the ability to change the generation laser wavelength over a range sufficient to carry out the desired chemical identification. If only a limited number of different wavelengths are required, devices like a Raman cell, a Brillouin cell, a multiple wavelength laser, or multiple lasers can be used. Any device or system giving the access to more than one wavelength should be considered as an embodiment of the method disclosed herein.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. A method of material analysis of a target object comprising:
   (a) creating ultrasonic displacements on a surface of a part of the target object by directing a generation laser beam at the part of the target;
   (b) varying the wavelength of the generation laser beam and creating ultrasonic displacements on the surface of the part of the target by directing the generation laser beam having the varied wavelength at the part of the target;
   (c) measuring the amplitude of the ultrasonic displacements of step (a) and step (b);
   (d) forming a plot of the wavelengths of the generation beams with the measured ultrasonic displacements;
   (e) providing a plot of wavelengths of generation laser beams versus ultrasonic displacements created by generation laser beams directed to a target of known composition; and
   (f) determining the target composition by comparing the plot of step (d) with the plot of step (e).

2. The method of claim 1, further comprising evaluating the target structural integrity by measuring the ultrasonic displacements of steps (a) and (b).

3. The method of claim 1, wherein the target comprises a manufactured part.

4. The method of claim 1, wherein the target comprises a manufactured part assembled onto a finished product.

5. The method of claim 1, further comprising estimating optical depths on the surface of the part based on the measured ultrasonic displacements of steps (a) and (b), forming a plot of the wavelengths of the generation beams versus the estimated optical depths, and combining the plot having the estimated optical depths with the plot of step (d).

6. The method of claim 1, further comprising forming a comparison data array of values of measured amplitudes of target surface displacement correlated to the wavelengths of the laser wave that created the displacement, where the target surface composition is known.

7. A method of analyzing an object comprising:
   (a) generating ultrasonic displacements on a part of the object using a pulsed generation laser beam operating at more than one known wavelength;
   (b) measuring the displacement amplitude on the part of the object generated at each known wavelength;
   (c) creating a measured data array comprising the displacement amplitude generated at each known wavelength and the corresponding known wavelengths;
   (d) comparing the measured data array to a data array obtained from a known material and that comprises measured values of acoustic displacements and the wavelengths of generation laser beams used to create the acoustic displacements; and
   (e) identifying the object composition based on the step of comparing the measured data array to the data array.

8. The method of claim 7, wherein the data array obtained from a known material is created by generating ultrasonic displacement in a sample of the known material using a generation laser over a range of wavelengths, measuring the displacements, and correlating the displacements to the laser wave wavelength.

9. The method of claim 7, wherein the data array obtained from a known material is created by a laboratory spectroscopic evaluation.

10. The method of claim 7, wherein the object is a manufactured part.

11. The method of claim 10, wherein the manufactured part is affixed to an aircraft.

12. A method of ultrasound inspection of a target object comprising;
   contacting a generation laser beam onto the target object;
   generating ultrasonic displacements on a part of the target object with the generation laser beam;
   measuring the ultrasonic displacements;
   varying the generation laser beam wavelength;
   generating additional ultrasonic displacements on the part of the target object with the generation laser beam at a different laser beam wavelength;
   measuring the additional ultrasonic displacements;
   forming a measured data array of ultrasonic displacements and generation laser beam wavelengths;
   correlating the measured ultrasonic displacements to the wavelength of the generation laser beam used to generate the displacement;
   comparing the measured data array to a data array of a known material;
   determining the target object material based on the step of comparing; and
   detecting defects in the target object by analyzing the ultrasound displacements.

13. The method of claim 12, further comprising scanning a substantial amount of the target object with the generation laser beam.

14. The method of claim 12, wherein the target object comprises a part assembled within a finished product.

* * * * *